United States Patent [19]

Zeller

[11] Patent Number: 5,285,797

[45] Date of Patent: Feb. 15, 1994

[54] PORTABLE BODY RESTRAINT DEVICE

[76] Inventor: Donald D. Zeller, 1962 Carrier Rd., Palo, Iowa 52324

[21] Appl. No.: 817,379

[22] Filed: Jan. 6, 1992

[51] Int. Cl.$^5$ .............................................. A61F 5/37
[52] U.S. Cl. .................................... 128/870; 128/869
[58] Field of Search ............... 128/870, 871, 875, 876, 128/869, 846

[56] References Cited

U.S. PATENT DOCUMENTS

| | | | |
|---|---|---|---|
| 2,675,564 | 4/1954 | Hughes | 128/870 |
| 3,650,523 | 3/1972 | Darby | 128/870 |
| 4,369,982 | 1/1983 | Hein | 128/870 |
| 4,854,305 | 8/1989 | Bremer | 128/870 |

Primary Examiner—Robert A. Hafer
Assistant Examiner—David Kenealy
Attorney, Agent, or Firm—James C. Nemmers

[57] ABSTRACT

A portable body restraint device for use in restraining and transporting prisoners or patients who are unmanageable. The device includes a flat, wide board sufficiently large to receive facedown the person to be restrained. The board is provided with properly positioned slots and adjustable straps that provide for restraining any person regardless of his or her size. The slots and adjustable straps permit the person's pelvis, chest, wrists, ankles, arms and legs to be secured as well as the person's head.

5 Claims, 3 Drawing Sheets

PORTABLE BODY RESTRAINT DEVICE

BACKGROUND OF THE INVENTION

Not infrequently, law enforcement officers and medical personnel must handle individuals who have become temporarily unmanageable due to a physical or mental condition or because of the use of drugs or alcohol. In such situations, it is the responsibility of the law enforcement officer or medical attendant to restrain the individual in order to prevent such individuals from damaging property, other persons, or even themselves. Also, once properly restrained, it is almost always necessary to transport the restrained individual to another location such as a hospital or confinement facility.

At the present time, various restraint devices are used. In the law enforcement area, these include handcuffs, shackles and straight jackets. However, persons confronted with arrest or confinement frequently are quite violent and jerk and move all of his or her body parts in an effort to escape. In so doing, they can cause injury to themselves and to the law enforcement officers and others. Since handcuffs will only restrain the wrists and shackles will only restrain the ankles, these restraining devices do not prevent such individuals from using their head or their complete body in an effort to escape. Moreover, handcuffs and shackles have the potential of injuring the prisoner's limbs if secured too tightly, and in any event, many state laws prohibit the use of handcuffs for the purpose of restraint if they are attached to a permanent fixture. Thus, these presently used devices and methods do not provide for complete and safe restraint of an individual nor do they assist in transporting the individual to a confinement or other facility.

In the medical field, there are known and used backboards which are designed to permit transportation of an injured person usually to a hospital or trauma center for treatment. Such persons may be conscious or unconscious, and in either event, it may be necessary to immobilize the person's head, a leg, arm, back etc. to prevent further injury to the person. Such devices are designed to provide for such partial immobilization and also to provide for ease of transportation to a hospital or trauma center.

At the present time, there are no devices or equipment available to provide for complete restraint and transportation of unmanageable individuals. Since the primary concern of law enforcement officers as well as medical personnel is the safety of the subject individual, there is an unmet need for a means of safely and completely restraining such individuals while providing for the transport of the individuals to a confinement or treatment facility.

There is also a need for a restraining device that provides for complete restraint but which is simple to use and which enables the subject to be easily placed in it without use of excessive force. Such a device also must be humane and safe for the subject and must be easily transportable and easily cleanable.

There is a further need for a restraining device that can also be used for limited periods of time to control the subject after the individual has been transported to a confinement or correctional facility. Such a device should minimize the staffing requirements during this temporary confinement period.

SUMMARY OF THE INVENTION

The body restraining device of the invention is a complete body restraint that consists of a flat, wide board with a plurality of slots properly positioned to receive adjustable straps so that the individual's head, pelvis, chest, wrists, ankles, arms and legs can be secured. The restraining device of the invention is designed to receive the individual facedown on the board, and once the individual is properly secured, restraint is sufficient to prevent any motion. Hand holes along the sides of the board provide for transportation of the board and individual, even in a vertical orientation, if necessary. The restraining device of the invention is sufficiently wide that the restrained person cannot roll over, and the positioning of the slots and straps is such that the device can be used to restrain any individual regardless of size.

DESCRIPTION OF THE PREFERRED EMBODIMENT OF THE INVENTION

Figure 1:
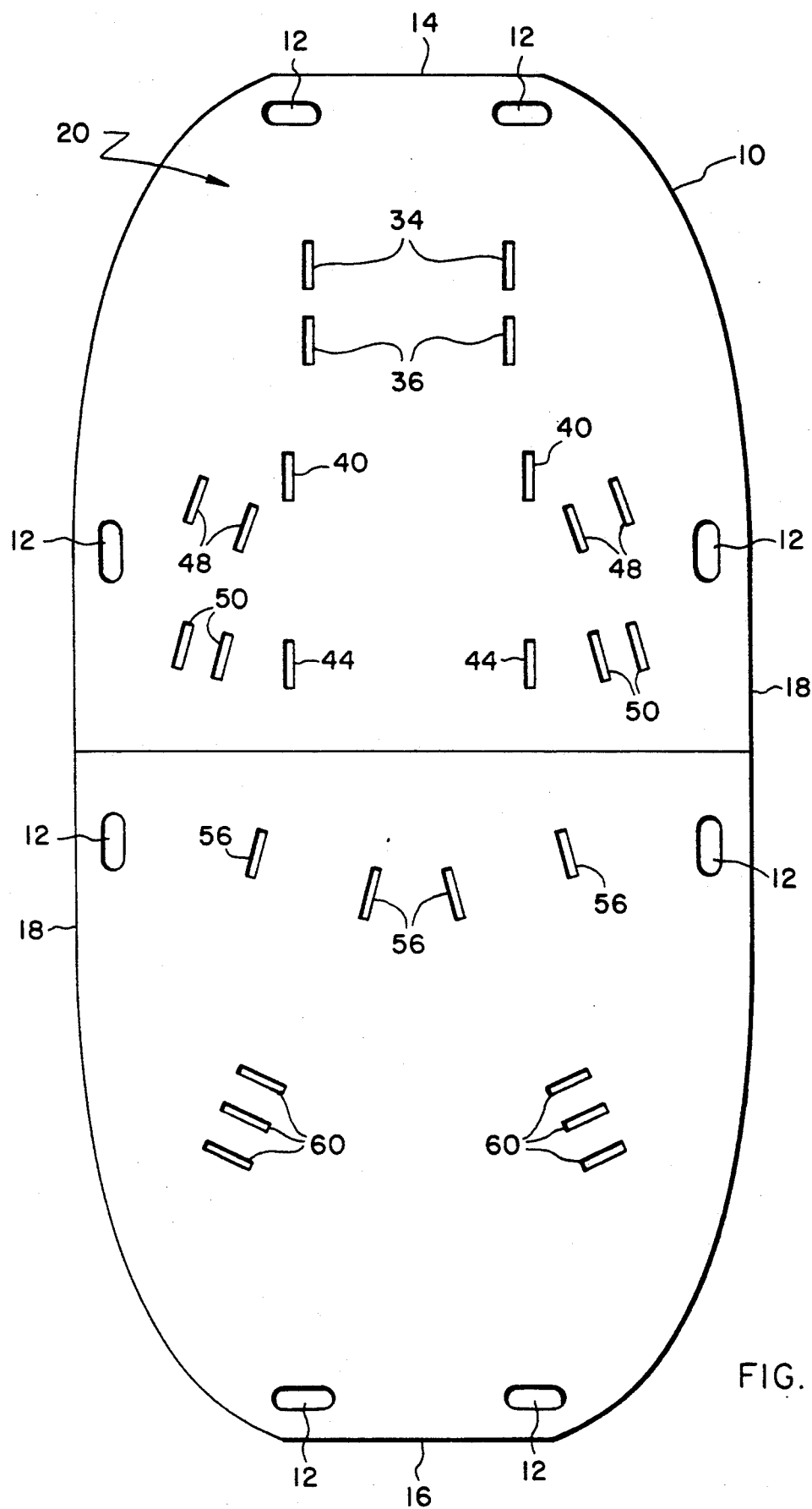
FIG. 1 is a top or plan view of a restraining device constructed according to the principles of the invention.

In the drawings, there is illustrated a board 10 that is relatively flat and of a sufficient size to receive the subject individual. For example, the board 10 may be approximately eight (8) feet long and four (4) feet wide and have rounded corners so as to present a somewhat elliptical shape. It should be understood, however, that the particular shape of the board is not essential to the purpose of the restraining device, but it is preferred that the corners be rounded so as to make the device easier to transport. The board 10 is sufficiently thick so as to be strong enough to carry individuals of all sizes and weights. Thickness of the board 10 will depend primarily upon the type of material used in making the board, which may be made of plywood or molded from plastic or fiberglass, the latter being lighter in weight without sacrificing strength.

The board 10 is provided with hand holes 12 around its periphery near the outer edge so that the board can be carried by two or more attendants. Preferably, a pair of hand holes 12 are provided near the top edge 14, near the bottom edge 16, and near each side edge 18. This permits up to four individuals to grasp the board 10 and transport it.

Figures 2, 4:
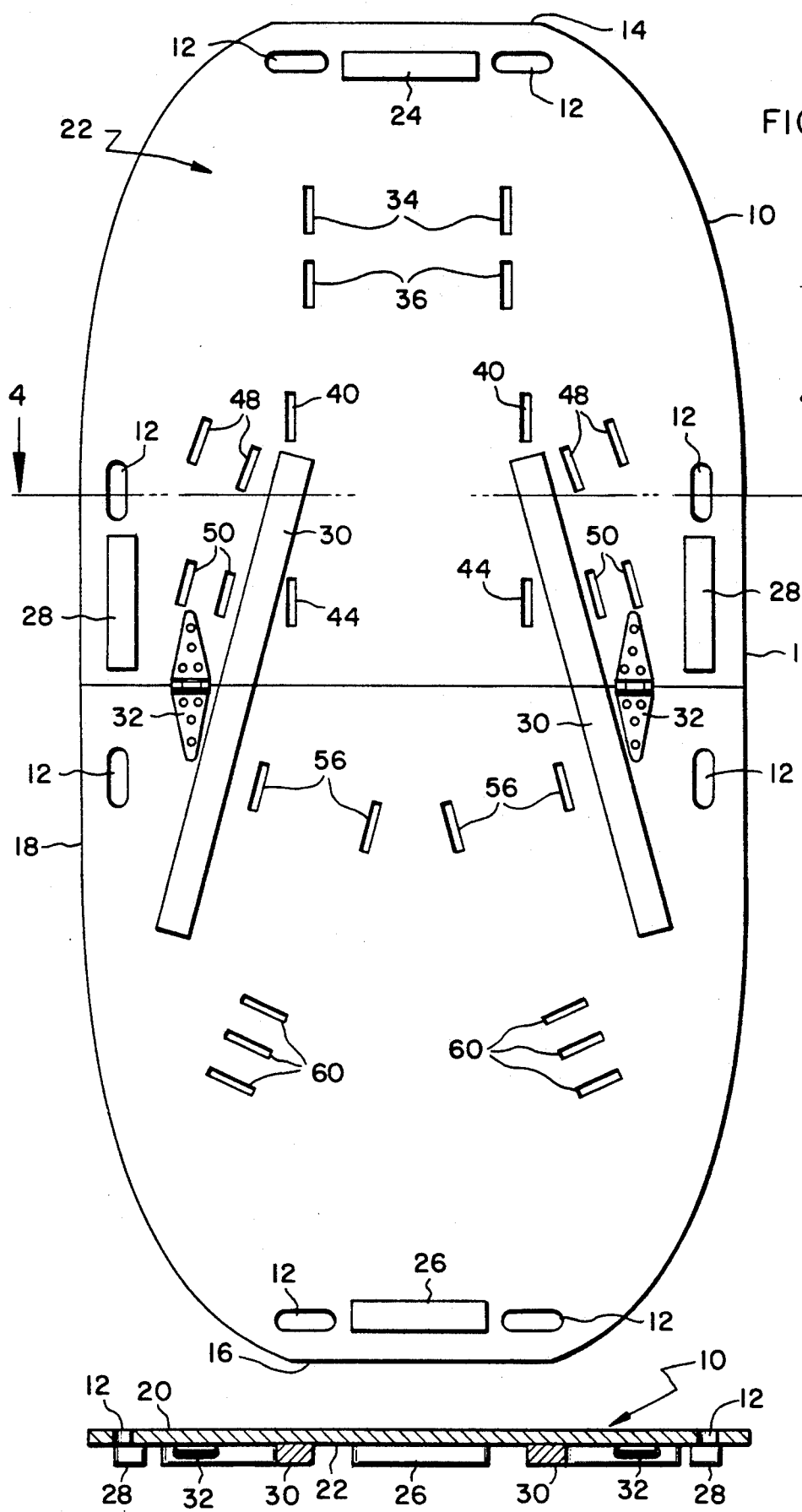
FIG. 2 is a plan view of the opposite side of the device of FIG. 1.
FIG. 4 is a sectional view taken on the line 4—4 of FIG. 2.

The top surface 20 of the board 10 is preferably smooth, nonporous and of material that is resistant to chemicals so as to be easily cleanable, since cleaners and disinfectants will be frequently used to keep the board clean. The bottom surface 22 (see FIG. 2) is provided with support members 24 and 26 that extend along the top edge 14 and bottom edge 16, respectively. Similarly, side support members 28 extend along the side edges 18. The support members 24, 26, 28 and 30 provide for spacing of the board 10 from the floor or other surface upon which it rests so as to facilitate grasping of the hand holes 12.

In addition, if desired, the board 10 can be provided in the middle with sliding hinges 32 so that the board 10 can be separated when not in use so as to occupy less storage space.

Figure 3:
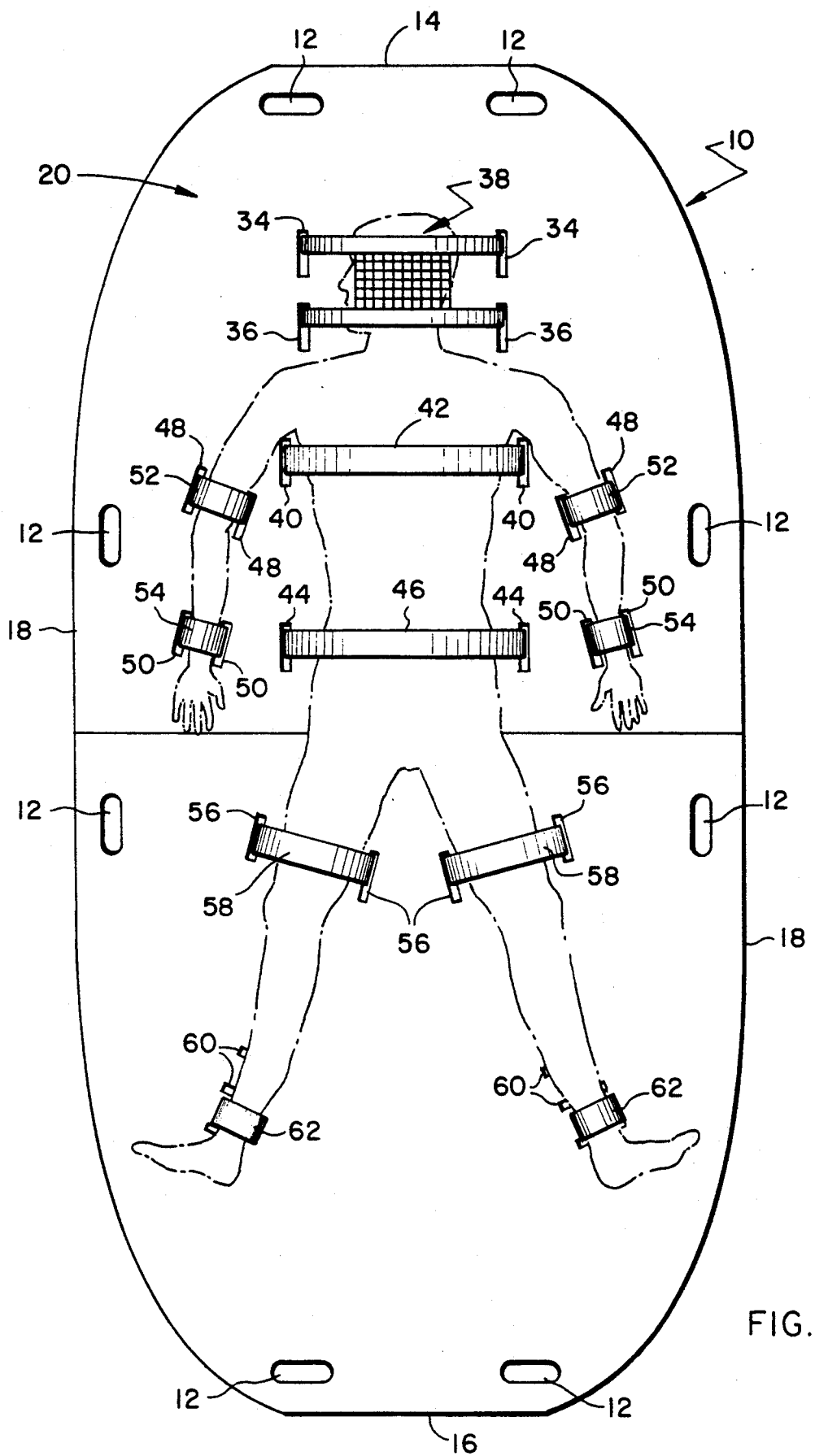
FIG. 3 is a top or plan view similar to FIG. 1 but illustrating a person placed and restrained on the device with the restraining straps in place.

In order to provide for securing of a person to the restraining board 10, the board 10 is provided with a plurality of slots for the receipt of adjustable restraining straps. Near the top edge 14 are a first pair of head slots 34 that are spaced apart a sufficient amount to accommodate a person's head between them. A second pair of head slots 36 are positioned just beneath the head slots 34. This allows head gear 38 (see FIG. 3) to secure a person's head between the head slots 34 and 36.

Below the head slots 34 and 36 and toward the center of the board 10 and spaced slightly wider apart are a pair of chest restraint slots 40. The slots 40 receive between them a chest restraint strap 42. Similarly, beneath the chest slots 40 and at approximately the center of the board 10 are a pair of spaced apart pelvis restraint slots 44 which receive a pelvis restraint strap 46.

Near the chest and pelvis restraint slots 40 and 44, but closer to the side edges 18 on each side of the board 10, are a pair of upper arm restraint slots 48 and a pair of wrist restraint slots 50. Each pair of the arm restraint slots 48 receives an arm restraint strap 52 while each pair of wrist restraint slots 50 receives a wrist strap 54.

Similarly, in the lower portion of board 10 there are two pairs of leg restraint slots 56, positioned so as to provide for restraining the legs of the person around his or her thighs. Each pair of slots 56 receives a leg restraint strap 58. Similar to the arm slots 48 and the wrist slots 50, the leg slots 56 are angled outwardly so as to permit the legs of the restrained individual to be separated.

At the bottom of the board 10 near its bottom edge 16 are ankle restraint slots 60. These slots can be arranged in pairs similar to the other slots which have been described. However, I have shown three slots on each side of the board which are used to restrain the person's ankles. The use of three slots 60 permits better adjustability in that an ankle strap 62 can be secured to selected pairs of the three slots 60.

Obviously, there are a variety and types of adjustable straps that can be used in connection with the restraining board of the invention. Numerous straps of various materials are commercially available. Preferably, the wrist straps 52 and ankle straps 62 are of leather or other material which can be positively locked at a selected one of a number of lengths. This is necessary so that the person cannot release himself. The straps other than the wrist straps 52 and ankle straps 62 may be adjustably joined by using Velcro fasteners.

Use of the restraining device of the invention is quick and simple and provides complete body restraint of the subject. The device is used by positioning the subject facedown on the board 10. The facedown position is essential in order to maintain a clear airway if the subject should become ill. The various straps are then secured first around the pelvis and chest and then around the arms, thighs, ankles and wrists of the person being restrained. If necessary, the subject's head is then also secured to the board 10 by head gear 38. After thus being secured, restraint of the individual is sufficient to prevent almost any movement, but the restrained individual is not uncomfortable. Once restrained, the individual on the board 10 is easily transported even if it is necessary to vertically orient the board 10 in order to move through doors, etc. Although the subject may be on the board 10 for a very short time only during transport by attendants, there may be situations where the subject will be restrained on the board 10 for several hours. In this event, the board 10 is sufficient wide that the subject cannot roll over and become injured. Restraint for this length of time is sometimes required in order to allow the effects of drugs or alcohol to wear off or to protect the individual until drugs are administered to subdue the individual when given by appropriate medical personnel.

Although I have described the device of the invention in connection with the preferred embodiment thereof, it will be evident to those skilled in the art that various revisions and modifications can be made to the embodiment described herein without departing from the spirit and scope of the invention. For example, precise positioning of the slots might be varied from the specific locations disclosed herein. Also, the particular shape of the board may be varied, but it is essential that the board be sufficiently wide to prevent the individual from rolling over when restrained on the board. Obviously, different types of restraining straps can be used, and although straps utilizing Velcro fasteners are preferred except for the wrist and ankles where leather restraints that lock are preferred, any type of adjustable straps may be used in connection with the invention. It is my intention that these, as well as other variations and modifications to the preferred embodiment and which are obvious to those skilled in the art, will be included within the scope of the following claims.

What is claimed is as follows:

1. A portable body restraint device for restraining combative or violent individuals by securing the individual's head, pelvis, chest, wrists, arms, legs and ankles, said device comprising a rigid board having a relatively flat top surface, a head portion at one end for underlying the head of an individual to be restrained and a foot portion at the end opposite the head portion for underlying the legs of the individual to be restrained, the board being longer than it is wide and being of a sufficient length and width to accommodate an individual of any size in the proper position for restraint with the individual face down longitudinally on the board with the arms of the individual slightly separated from the body and the legs spread apart, a body portion intermediate the head portion and the foot portion for underlying the chest and pelvis of the individual to be restrained, a pair of slots one slot on each side of a properly positioned individual's head in the head portion of the board, a pair of slots one on each side of a properly positioned individual's chest and pelvis in the body portion of the board, a pair of slots one on each side of a properly positioned individual's wrists and arms in the body portion, a pair of slots one slot on each side of a properly positioned individual's upper legs in the foot portion, the slots for the head, chest, pelvis, wrists, arms and upper legs extending generally longitudinally of the board, at least one pair of slots beneath each one of a properly positioned individual's ankles in the foot portion of the board which ankle slots extend generally transversely of the board, there being more than one pair of slots in the foot portion for each ankle to provide for individuals of different heights, straps extending through each pair of slots so as to be engageable with respective ones of the individual's body parts to hold the individual securely on the board, a plurality of hand grips extending along the sides of the board to provide for carrying of the board, and support members on the bottom surface of the board to provide for spacing the board from a surface upon which it rests so as to facilitate grasping of the hand grips.

2. The portable body restraint device of claim 1 in which means is provided to cover and thus restrain the individual's head when turned sideways.

3. The portable body restraint device of claim 2 in which the means for restraining the head of the individual includes a head gear that is secured to the board and covers a portion of the individual's head to hold it in place with the head turned sideways.

4. The portable body restraint device of claim 3 in which the top surface of the board is smooth and nonporous to liquids.

5. The portable body restraint device of claim 4 in which the hand grips are hand holes extending through the board along the edges of the board.

* * * * *